United States Patent [19]
Podlesak

[11] Patent Number: 5,596,279
[45] Date of Patent: Jan. 21, 1997

[54] APPARATUS AND METHOD FOR INDICATING ELECTRICAL BREAKDOWN IN WATER COOLING SYSTEMS

[75] Inventor: Thomas F. Podlesak, Oakhurst, N.J.

[73] Assignee: The United States of America as represented by the Secretary of the Army, Washington, D.C.

[21] Appl. No.: 292,139

[22] Filed: Aug. 17, 1994

[51] Int. Cl.$^6$ .................................................. G01N 27/06
[52] U.S. Cl. .......................................... 324/439; 324/718
[58] Field of Search ...................... 324/425, 439, 324/522, 555, 713, 718

[56] References Cited

U.S. PATENT DOCUMENTS

| | | | |
|---|---|---|---|
| 4,491,798 | 1/1985 | Palmer et al. | 324/425 |
| 4,853,638 | 8/1989 | Endou et al. | 324/441 |
| 4,881,037 | 11/1989 | Bellingham et al. | 324/425 |
| 4,975,154 | 12/1990 | Palmer et al. | 324/439 X |
| 5,374,380 | 12/1994 | James | 324/439 X |
| 5,435,909 | 7/1995 | Burrows | 324/439 X |

*Primary Examiner*—Maura K. Regan
*Assistant Examiner*—Glenn W. Brown
*Attorney, Agent, or Firm*—Michael Zelenka; George B. Tereschuk

[57] ABSTRACT

A method for indicating electrical breakdown in a nonconductive water cooling system for high power electrical equipment at an early stage so as to avoid the danger of accidental faults. The method utilizing a small resistor to generate a detectable voltage when the resistance of the water breaks down, thus degrading from a nonconductive to a conductive state. Once a voltage is detected, the electrical equipment is shut down until the cooling water is made nonconductive again. An apparatus for indicating electrical breakdown in a water cooling system for high power electrical equipment is also provided.

10 Claims, 1 Drawing Sheet

APPARATUS AND METHOD FOR INDICATING ELECTRICAL BREAKDOWN IN WATER COOLING SYSTEMS

GOVERNMENT INTEREST

The invention described herein may be manufactured, used, and licensed by or for the government of the United States of America for governmental services without the payment to us of any royalty thereon.

FIELD OF THE INVENTION

This invention relates to the field of pulse power technology, and more specifically to a method of detecting electrical breakdown in the water cooling lines of high voltage electrical equipment.

BACKGROUND OF THE INVENTION

Since power semiconductors dissipate a great deal of heat, there is and has been a need for a means to cool such components to avoid overheating and thus avoid breakdown of the system in which the power semiconductors operate. Heretofore, such power semiconductors have been liquid cooled with either an insulating-type liquid or purified water. Cooling liquids such as insulating liquids and purified water have been used because it is believed that such liquids are not and do not become conductive during operation, and thus prevent the danger of an accidental fault or operation, and thus prevent the danger of an accidental fault or breakdown of the system in which the power semiconductors operate.

It has been found, however, that insulating liquids are not very efficient heat dissipators and thus are not as desirable as water for cooling such systems. Moreover, it has been found that water is only an excellent insulator in its nonconductive state, and that since water is a universal solvent it is very easy for nonconductive water to quickly enter into an impure, or electrically conductive state, because another attribute of water's being a universal solvent is that it will dissolve almost any substance over time, including substances which make water conductive. This can have catastrophic effects on the high power semiconductor equipment of interest. As a result, there is a need for a way of immediately indicating when such nonconductive water in a cooling system degrades to a conductive state so that the cooling system can be shut down to make the water nonconductive, and thus immediately prevent catastrophic system breakdown.

SUMMARY OF THE INVENTION

Accordingly, the present invention provides apparatus and methods for indicating the conductive degradation of water used in cooling systems of high power electrical equipment so as to cause immediate shut-down and enable early repair of the cooling system and avoid the danger of accidental system faults. To attain this, the present invention encompasses apparatus and methods providing a fault-indicating water resistor intrinsic to the water-filled cooling lines such that when the water degrades to a conductive state, current passes through the water resistor indicating that such electrical breakdown due to conductive degradation has occurred.

In a preferred embodiment of the apparatus of the present invention, wherein the cooling system comprises at least two chillblocks positioned on either side of a power semiconductor having a plurality of water pipes circulating through each chillblock, the means for immediately indicating conductive degradation of the water comprises a resistor electrically connected between the water entering the intake pipe of each chillblock such that any current induced in the water due to conductive degradation can be readily electrically indicated through creating voltage across the resistor, thus indicating the electrical breakdown of the insulating properties of the previously non-conductive water. Once such electrical breakdown is indicated, the entire power semiconductor system can be immediately shut-down without operator interpretation of measurements or readings or other operator involvement and the water can be made non-conductive.

These and other features of the invention are described in more complete detail in the following description of the preferred embodiment when taken with the drawing. The scope of the invention, however, is limited only by the claims appended hereto.

DETAILED DESCRIPTION OF THE INVENTION

Figure 1:
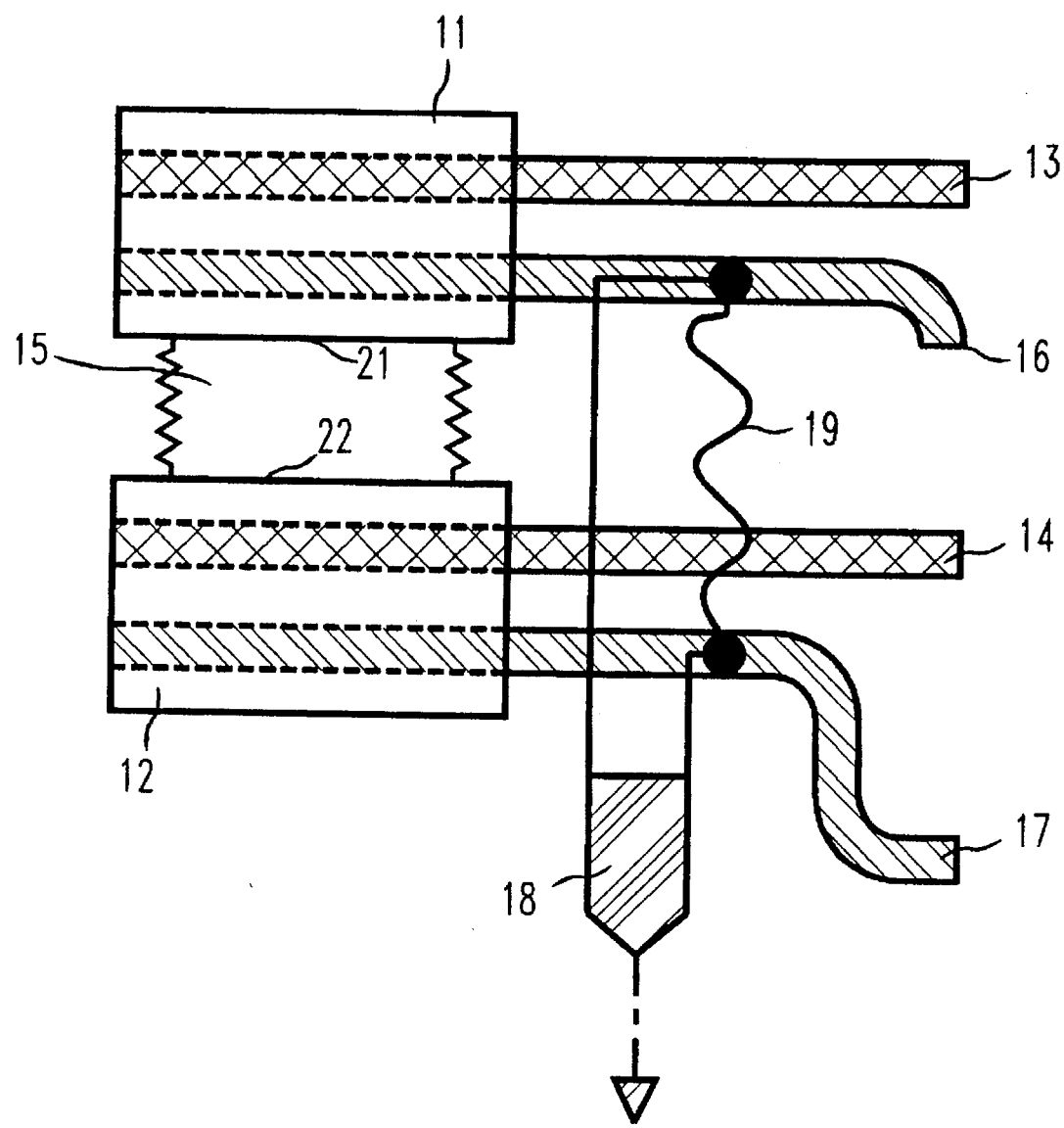
FIG. 1 is a pictorial view of a preferred embodiment of the invention.

Referring now to FIG. 1, there is shown high power semiconductor 15 having upper terminal 21 and lower terminal 22. Chillblock 11 has water flowing through its interior from an intake pipe 16 to an output pipe 13. Similarly, said chillblock 12 has water flowing from an intake pipe 17 to an output pipe 14. To provide a means for indicating when the water starts to degrade to a conductive state and thus allow electrical breakdown, a fault indicating water resistor 19 is intrinsically formed between the water in said intake pipe 16 and said intake pipe 17. A detector circuit 18 is electrically coupled to said resistor 19 to immediately indicate if any measurable current passes through said resistor 19 thus also indicating that the water has degraded to a conductive state. Similarly, chillblock 12 has water flowing from intake pipe 14 to output pipe 17. To provide a means for detecting when the purified water starts to become conductive and thus breakdown, fault indicating resistor or resistor 19 is electrically connected between the purified water in output pipe 16 and output pipe 17. Detector circuit 18 is electrically coupled to resistor 19 to detect if any current passes through resistor 19 thus indicating that the purified water has become conductive.

In operation, water passes through said chillblocks 11 and 12 through said intake pipes 16 and 17, respectively, to output pipes 13 and 14, respectively. Since said chillblocks 11 and 12 make physical contact with said high power semiconductor 15, heat is removed from the semiconductor package and carried away in the water through heat exchange principles. Connecting the water flowing through said intake pipe 16 with said intake pipe 17 with a small resistor establishes a resistor network, wherein current can flow from the first of said chillblocks 11 through the water in the intake pipe 16 to said resistor 19 to the water in the other intake pipe 17, through the water in the second intake pipe 17 back into the second chillblock 12, thus completing an electrical circuit between terminals 21 and 22, respectively, of said semiconductor 15. Since chillblocks 11 and 12 make physical contact with high power semiconductor 15, heat is removed from the semiconductor package and carried away in the purified water. Connecting the water flowing through output pipe 16 with output pipe 17 with a small resistor on the order of 1 ohm establishes a resistor network, wherein current can flow from one chillblock through the water in the respective output pipe to resistor 19, through resistor 19 to the water in the other output pipe, through the water in the second output pipe back into the second chillblock, thus completing the circuit between terminals 21 and 22 of semiconductor 15.

Since under normal circumstances the resistance of water is very high (thousands of ohms), very little current will flow through the resistor network. Thus, tying pipes 16 and 17 together with resistor 19 which is on the order of 1 ohm, the water in both pipes will be at the same electrical potential, thus precluding current from flowing from point to point within the cooling system. This provides additional insurance that a fault will not develop in the system. A similar procedure can be applied to output pipes 13 and 14.

If the water suffers electrical breakdown due to conductive degradation, its resistance decreases substantially, and its conductivity increases substantially thus allowing a large electrical current to flow through the cooling system. Once a current flows in the water, it will tend towards the path of lowest resistance which is through small resistor 19. As a result, a voltage will be created across resistor 19. This voltage can be indicated by detector circuit 18 which may be used to initiate an emergency procedure, shutting down the apparatus before damage could be done.

As a result, resistor 19 should be placed in a location such that it does not create a parallel path for the electric current to flow around the semiconductor. This will insure that only the decreased resistance of the water will cause conduction in the cooling system, rather than the low resistance of resistor 19. Moreover, the value of resistor 19 is not limited to 1 ohm. It can be an value as long as it is small compared to the resistance of the water and it is large enough to produce a recognizable voltage signal across the resistor to trigger the indicator circuit.

The apparatus and methods of the present invention for indicating electrical breakdown in water cooling lines is not strictly limited to this type of system. Similar types of fault indicating resistors can be placed between two or more pieces of apparatus having a large difference in electrical potential between them that are connected via a water column. Other combinations of connecting the intake pipes 16 and 17, respectively, and output pipes 13 and 14, respectively, with,each other are also possible and are considered to be within the scope of this disclosure and the appended claims. Of course, it should be understood that the foregoing disclosure relates only to a small number of preferred embodiments of the apparatus of the present invention and that numerous modifications or alterations may be made therein without departing from the spirit and scope of the inventions as set forth in the foregoing disclosure and the appended claims.

The present invention also encompasses a number of methods of indicating electrical breakdown in water cooling systems, utilizing the previously described configurations. The method comprises the steps of selecting a plurality of portions of the cooling system being physically connected by a water column and having a large electrical potential between them, connecting an resistor between said selected portions of the cooling system, said resistor having a resistance value less than the water's resistance but large enough to produce a recognizable voltage signal when the resistance of said water degrades to a conductive state, coupling a detector circuit to said resistor to immediately indicate if a recognizable voltage signal passes through said resistor thus indicating that the water has degraded to a conductive state. Variations of this method similar to those described with the apparatus, such as using a one ohm resistor and modifying the connections between intake and output pipes, are also achievable and considered within the scope of this disclosure and the appended claims.

Accordingly, having shown and described what are at present considered to be the preferred and several embodiments of apparatus and methods of this invention, it should be understood that the same have been shown by way of illustration and not limitation. It should be understood, of course, that the foregoing disclosure relates only to a small number of preferred embodiments of the apparatus and methods of the present invention and that numerous modifications or alterations may be made therein without departing from the spirit and scope of the inventions as set forth in the foregoing disclosure and the appended claims. All modifications, alterations and changes coming within the spirit and scope of the invention are hereby meant to be included.

What is claimed is:

1. A method for indicating electrical breakdown in a water cooling system for high power electrical equipment, comprising the steps of:

selecting a plurality of portions of said water cooling system, said plurality of portions having a large electrical potential difference between them, being connected by a column of water, said water having a given resistance value that is nonconductive, connecting a resistor between at least two of said plurality of portions, said resistor having an ohmic value that is small compared to said given resistance value of the water and large enough to produce a recognizable voltage signal when the given resistance value of the water degrades to a conductive state;

coupling a detector circuit to said resistor, said detector circuit being capable of indicating when said recognizable voltage is present across said resistor; and shutting down said high power electrical equipment when said detector circuit indicates said recognizable voltage signal is present across said resistor.

2. The method for indicating electrical breakdown in water cooling systems for high power electrical equipment, as recited in claim 1, wherein two of said plurality of portions of the water cooling system selected are a pair of intake pipes.

3. The method for indicating electrical breakdown in water cooling systems for high power electrical equipment, as recited in claim 2, wherein said resistor is no greater than one ohm.

4. The method for indicating electrical breakdown in water cooling systems for high power electrical equipment, as recited in claim 1, wherein two of said plurality of portions of the water cooling system selected are a pair of output pipes.

5. The method for indicating electrical breakdown in water cooling systems for high power electrical equipment, as recited in claim 4, wherein said resistor is no greater than one ohm.

6. An apparatus for indicating electrical breakdown in a water cooling system for high power electrical equipment, comprising:

said water cooling system having a plurality of portions being connected by a column of water, said water having a given resistance value that is nonconductive;

a resistor connected between at least two of said plurality of portions having a large potential difference between them;

said resistor having an ohmic value that is small compared to said given resistance value of the water and large enough to produce a recognizable voltage signal when said given resistance value of the water degrades to a conductive state;

a detector circuit coupled to said resistor, said detector circuit being capable of indicating when said recognizable voltage signal is present across said resistor; and a means for shutting down said high power electrical equipment when said detector circuit indicates said recognizable voltage signal across said resistor.

7. An apparatus for indicating electrical breakdown in water cooling systems for high power electrical equipment, as recited in claim 6, wherein two of said plurality of portions of the water cooling system are a pair of intake pipes.

8. An apparatus for indicating electrical breakdown in water cooling systems for high power electrical equipment, as recited in claim 7, wherein said resistor is no greater than one ohm.

9. An apparatus for indicating electrical breakdown in water cooling systems for high power electrical equipment, as recited in claim 6, wherein two of said plurality of portions of the water cooling system are a pair of output pipes.

10. An apparatus for indicating electrical breakdown in water cooling systems for high power electrical equipment, as recited in claim 9, wherein said resistor is no greater than one ohm.

* * * * *

UNITED STATES PATENT AND TRADEMARK OFFICE
CERTIFICATE OF CORRECTION

PATENT NO : 5,596,279
DATED : Jan. 21, 1997
INVENTOR(S): Thomas F. Podlesak

It is certified that error appears in the above-identified patent and that said Letters Patent is hereby corrected as shown below:

column 2, delete lines 42-50 after "state.";

column 2, delete lines 65-68 and column 3, lines 1-9 after "semiconductor 15.";

Signed and Sealed this

Tenth Day of February, 1998

Attest:

BRUCE LEHMAN

Attesting Officer

Commissioner of Patents and Trademarks